US011285036B2

(12) United States Patent
Honda

(10) Patent No.: US 11,285,036 B2
(45) Date of Patent: Mar. 29, 2022

(54) INTRAVAGINAL SUPPORT DEVICE, FLUID INJECTION DEVICE, AND TREATING METHOD FOR PELVIC ORGAN PROLAPSE BY USE OF INTRAVAGINAL SUPPORT DEVICE

(71) Applicant: TERUMO KABUSHIKI KAISHA, Tokyo (JP)

(72) Inventor: Kei Honda, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 1326 days.

(21) Appl. No.: 14/874,904

(22) Filed: Oct. 5, 2015

(65) Prior Publication Data

US 2016/0022475 A1  Jan. 28, 2016

Related U.S. Application Data

(63) Continuation of application No. PCT/JP2013/002379, filed on Apr. 5, 2013.

(51) Int. Cl.
    *A61F 6/12*  (2006.01)
    *A61F 2/00*  (2006.01)
    *A61F 6/08*  (2006.01)

(52) U.S. Cl.
    CPC .............. *A61F 6/12* (2013.01); *A61F 2/005* (2013.01); *A61F 6/08* (2013.01); *A61F 2210/0061* (2013.01)

(58) Field of Classification Search
    CPC ...... A61F 6/00; A61F 6/06; A61F 6/08; A61F 6/12; A61F 6/14; A61F 6/16; A61F 6/18;
    (Continued)

(56) References Cited

U.S. PATENT DOCUMENTS 2,101,273 A * 12/1937 Smith .................... A61H 21/00
                                                          601/18
2,638,093 A *  5/1953 Kulick ................... A61B 1/32
                                                          600/29
(Continued)

FOREIGN PATENT DOCUMENTS

DE   37 00 239 A1   9/1987
EP   0 663 197 A1   7/1995
(Continued)

OTHER PUBLICATIONS

International Search Report (PCT/ISA/210) dated May 7, 2013, by the Japanese Patent Office as the International Searching Authority for International Application No. PCT/JP2013/002379.
(Continued)

*Primary Examiner* — Michelle J Lee
(74) *Attorney, Agent, or Firm* — Buchanan Ingersoll & Rooney PC

(57) ABSTRACT

An intravaginal support device is disclosed, which is capable of being expanded and contracted in a state of being inserted in a vagina for treating pelvic organ prolapse. The intravaginal support device can include an opening/closing portion capable of switching operations between an open state for allowing passage of fluid therethrough and a cut-off state for cutting off passage of the fluid, a bag portion being expandable by flowing-in of fluid through the opening/closing portion and being contractible by flowing-out of the fluid through the opening/closing portion, and an insertion guide portion adapted to guide the bag portion into the vagina, the insertion guide portion extending along at least part of an outer surface of the bag portion from a vaginal orifice side end portion of the bag portion to a vaginal depth side end portion of the bag portion.

20 Claims, 12 Drawing Sheets

(58) Field of Classification Search
CPC ........ A61F 6/146–18; A61F 2/00–0013; A61F 2/0022–005; A61F 2210/00; A61F 2210/0061; A61B 17/12022–12045; A61B 17/12136; A61B 17/12099; A61B 17/12104; A61B 17/12131; A61B 2017/1205; A61B 2017/12081
See application file for complete search history.

(56) References Cited

U.S. PATENT DOCUMENTS

| | | | | |
|---|---|---|---|---|
| 4,669,478 | A * | 6/1987 | Robertson | A61F 6/08 600/300 |
| 4,709,690 | A * | 12/1987 | Haber | A61F 2/004 128/DIG. 25 |
| 5,609,559 | A * | 3/1997 | Weitzner | A61F 2/005 600/29 |
| 5,771,899 | A * | 6/1998 | Martelly | A61F 2/005 128/830 |
| 5,934,279 | A | 8/1999 | Lammers | |
| 6,470,890 | B1 | 10/2002 | Diokno et al. | |
| 2007/0089750 | A1 * | 4/2007 | Astani | A61F 2/005 128/830 |
| 2009/0216071 | A1 * | 8/2009 | Zipper | A61F 2/0009 600/29 |
| 2009/0266367 | A1 | 10/2009 | Ziv et al. | |
| 2013/0025604 | A1 | 1/2013 | Harmanli | |
| 2014/0243584 | A1 * | 8/2014 | Bercovich | A61F 6/08 600/29 |

FOREIGN PATENT DOCUMENTS

| | | |
|---|---|---|
| WO | 2010/114577 A1 | 10/2010 |
| WO | 2012/006670 A1 | 1/2012 |

OTHER PUBLICATIONS

Office Action dated May 10, 2016 by the Japanese Patent Office in corresponding Japanese Patent Application No. 2015-509607 (4 pages).

* cited by examiner

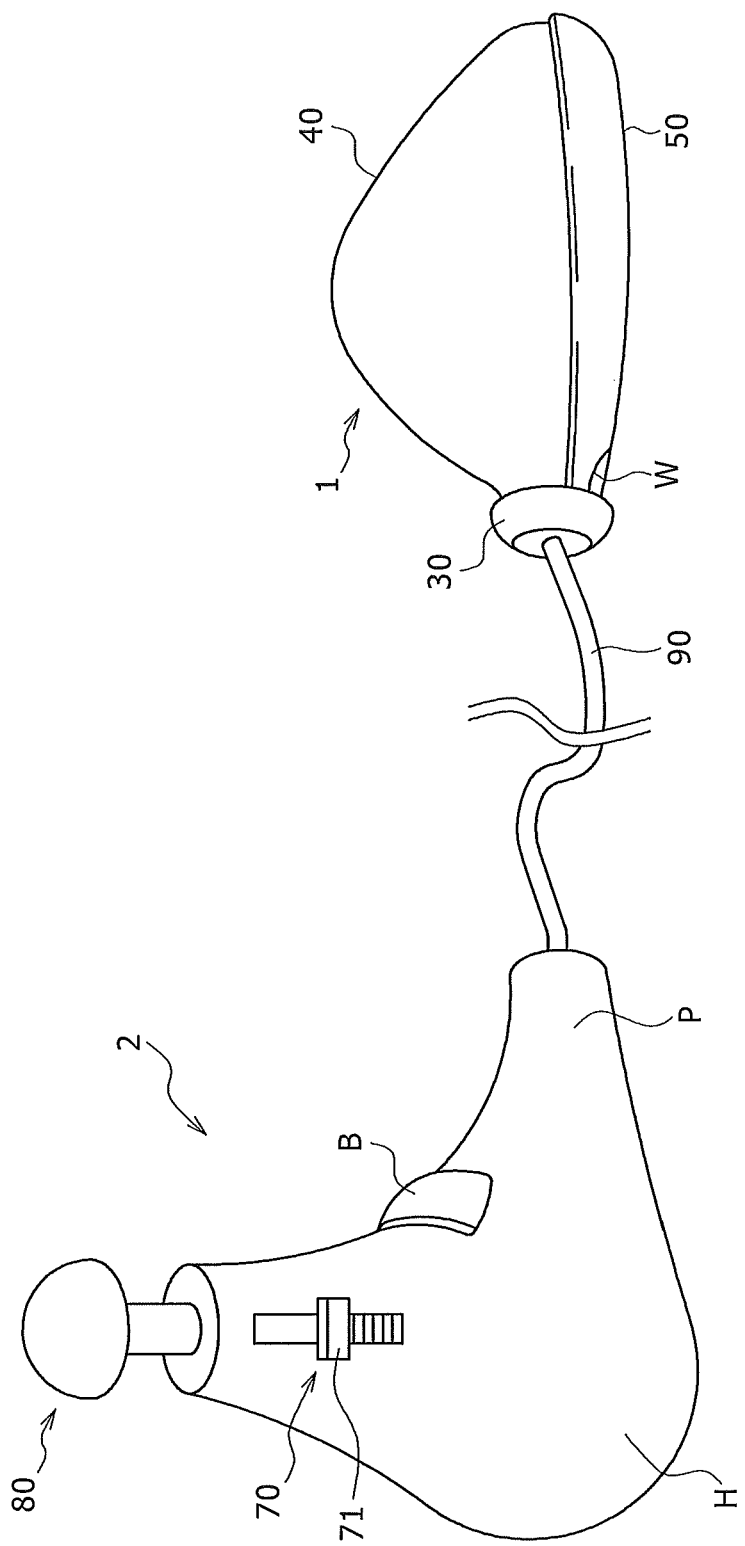

INTRAVAGINAL SUPPORT DEVICE, FLUID INJECTION DEVICE, AND TREATING METHOD FOR PELVIC ORGAN PROLAPSE BY USE OF INTRAVAGINAL SUPPORT DEVICE

CROSS-REFERENCES TO RELATED APPLICATIONS

This application is a continuation of International Application No. PCT/JP2013/002379 filed on Apr. 5, 2013, the entire content of which is incorporated herein by reference.

TECHNICAL FIELD

The present disclosure relates to an intravaginal support device which can be expanded and contracted in the state of being inserted in a vagina and which is used for treatment of pelvic organ prolapse. More particularly, the disclosure relates to an improvement in the intravaginal support device so as to facilitate the insertion into the vagina and to help retain the device in the patient's vagina. In addition, the present disclosure relates to a fluid injection device for expanding the intravaginal support device, more particularly to an improvement in the fluid injection device for facilitating a fluid injection operation.

BACKGROUND DISCUSSION

In the ageing of society, the number of cases of pelvic organ prolapses has been increasing. The pelvic organ prolapse is a disease in which an organ such as uterus, bladder, and rectum droops, and, in serious cases, prolapses to the outside of the body. The pelvic organ prolapse produces such symptoms as a keen discomfort, urinary disturbance, dyschezia, and pain in the prolapsed part. Attendant on ageing, the onset of these diseases is seen in 44% of the females having experienced vaginal delivery, the number of potential cases in Japan reaches 3.5 million, and that in USA reaches 7.7 million according to a report.

For mild cases of pelvic organ prolapses, effective are such therapeutic methods as pelvic floor muscle exercise, hormone replacement therapy, and coping treatments such as the use of a cushion integrated with underwear. For moderate and serious cases of pelvic organ prolapses, operative treatments such as mesh insertion and surgical fixation may be used according to the symptom and the patient's request. In addition, minimally invasive nonoperative treatments such as using a pessary are also practiced. A pessary can be composed of an elastically deformable ring body, which is inserted into and placed in the patient's vagina by a doctor, so as to support the drooping uterine neck, vaginal anterior wall, and vaginal posterior neck, thereby inhibiting pelvic organ prolapse.

In the case of a ring pessary, a circular ring body is inserted into the vagina in the state of being deformed into an elliptic shape. While the inserted ring body recovers from the elliptic shape into the original circular shape, the radial direction of the circular ring body thus recovered is set substantially perpendicular to the direction of going from the vaginal orifice toward the depth of the vagina. During this process, part of the ring body is pressed against that region of the vaginal anterior wall which is in the vicinity of a pubis-derived rigid tissue (hereinafter referred to as "pubic tissue") and on the uterine neck side. In that region, the part of the ring body is locked onto the pubic tissue through the vaginal anterior wall, whereby the ring body is retained in the vagina. For example, when the vaginal anterior wall is pushed in to the inner side of the body (to the urethra side), the surrounding flexible vaginal wall part can be deformed under pushing-in. In the region where the pubic tissue is present in a deep part, for example, pushing-in deformation in excess of the depth to reach the pubic tissue can be difficult. Therefore, when a pessary is pressed against that region of the vaginal anterior wall which is a little on the vaginal depth side than the region where the pubic tissue is present in the deep part (namely, that region of the vaginal anterior wall which is in the vicinity of the pubic tissue and on the uterine neck side described herein above), a recess is formed between the region where pushing-in deformation is possible and the region where pushing-in deformation can be difficult, and the pessary is locked in the recess. When a force in the direction of going from the depth of the vagina toward the vaginal orifice is exerted on the pessary in this locked state, a resisting force in the direction of going from the vaginal orifice toward the depth of the vagina is applied to the pessary from the pubic tissue through the vaginal anterior wall. Consequently, the pessary is inhibited from being dislodged.

When such a pessary is left in the body for a long period of time, an unpleasant smell can be generated, or bleeding occurs from the compressed part. Therefore, it can be necessary to periodically remove the pessary from inside the body, and then a cleaned pessary must be again inserted into and placed in the vagina, or a new pessary must be inserted into and placed in the vagina. However, the pessary has a ring body outside diameter much greater than the vaginal orifice, so that it is not easy for the patient herself to place and remove the pessary in daily use. In view of this, an intravaginal support device capable of being expanded and contracted within a vagina has been proposed as a substitute for a pessary.

For example, U.S. Pat. No. 6,470,890 discloses an intravaginal support device including an expandable, hollow, roughly donut-shaped inflatable portion; and a guide portion formed with an annular recess capable of accommodating the inflatable portion. The guide portion is formed therein with an air admission channel which has one end communicating with the inside space of the inflatable portion and is provided with a check valve at the other end. Air is introduced into the inflatable portion through the check valve by an air injection device, whereby the inflatable portion is inflated so that the intravaginal support device is retained inside the vagina.

The intravaginal support device as described in U.S. Pat. No. 6,470,890, however, has the problem that the intravaginal support device as a whole can be large and stiff, so that it cannot be said that the intravaginal support device is easy to be inserted into a vagina. Therefore, effort may be needed to insert or re-place the intravaginal support device. While the inflatable portion is provided in the periphery of the intravaginal support device for the purpose of retaining the intravaginal support device inside the vagina, the introduction of air leads to uniform inflation (or deflation) of the inflatable portion as a whole. Thus, variations in shape in conformity with the internal shape of a vagina cannot necessarily be achieved. For this reason, there have been cases in which retention of the intravaginal support device inside the vagina is insufficient, or a sufficient inhibitory effect on pelvic organ prolapse cannot be attained, or a compressed part is generated with the result of such troubles as bleeding and erosion.

SUMMARY

An intravaginal support device is disclosed, which can be easily inserted into a vagina and which can be securely retained in a patient's vagina.

A fluid injection device is disclosed, which can expand the intravaginal support device and which offers an easy fluid injection operation.

A treating method is disclosed for pelvic organ prolapse by use of a fluid injection device, which is for expanding the intravaginal support device and which offers a relatively easy fluid injection operation.

An intravaginal support device is disclosed, which is capable of being expanded and contracted in a state of being inserted in a vagina for treating pelvic organ prolapse including an opening/closing portion, a bag portion, and an insertion guide portion. The opening/closing portion is capable of switching operations between an open state for allowing passage of fluid therethrough and a cut-off state for cutting off passage of the fluid. The bag portion is expandable by flowing-in of fluid through the opening/closing portion, and is contractible by flowing-out of the fluid through the opening/closing portion. The insertion guide portion is adapted to guide the bag portion into the vagina, and extends along at least part of an outer surface of the bag portion from a vaginal orifice side end portion of the bag portion to a vaginal depth side end portion of the bag portion.

Note that the "fluid" refers to a fluid such as, for example, air, other gases, liquids, and viscose materials.

Here, in the intravaginal support device as above, preferably, for example, the insertion guide portion promotes expansion of the bag portion in the direction of a vaginal anterior wall.

In the intravaginal support device, preferably, the insertion guide portion is bent in the direction of the vaginal anterior wall, from the vaginal orifice side toward the vaginal depth side.

In the intravaginal support device, preferably, for example, the insertion guide portion has a covering portion for covering the vaginal depth side end portion of the bag portion.

In the intravaginal support device, preferably, the insertion guide portion is provided, at a vaginal orifice side end portion thereof, with a locking piece for locking to pubic tissue through a vaginal anterior wall.

In accordance with an exemplary embodiment, preferably, the intravaginal support device further includes a ring-shaped pressing portion surrounding the opening/closing portion, and has a configuration wherein the opening/closing portion has a check valve which allows fluid to flow into the bag portion but inhibits the fluid from flowing out of the bag portion, and the check valve allows the fluid to flow out of the bag portion when the ring-shaped pressing portion is pressed inward at a predetermined circumferential position.

In the intravaginal support device, preferably, for example, the ring-shaped pressing portion is contiguous with a vaginal orifice side end portion of the insertion guide portion.

A fluid injection device is disclosed for expanding an intravaginal support device capable of being expanded and contracted in a state of being inserted in a vagina for treating pelvic organ prolapse including an opening/closing portion, a bag portion, and an insertion guide portion. The opening/closing portion is capable of switching operations between an open state for allowing passage of fluid therethrough and a cut-off state for cutting off passage of the fluid. The bag portion is expandable by flowing-in of fluid through the opening/closing portion, and is contractible by flowing-out of the fluid through the opening/closing portion. The insertion guide portion is adapted to guide the bag portion into the vagina, and extends along at least part of an outer surface of the bag portion from a vaginal orifice side end portion of the bag portion to a vaginal depth side end portion of the bag portion. The fluid injection device can include an injection portion, an adjusting operation portion, and an injection operation portion. The injection portion is connected to the intravaginal support device and has an injection port, which communicates with the opening/closing portion. The adjusting operation portion is capable of adjusting the amount of fluid fed to the injection port of the injection portion. The injection operation portion feeds the fluid in an amount adjusted by the adjusting operation portion under pressure to the injection port of the injection portion.

A treating method is disclosed for mitigating a symptom of pelvic organ prolapse including inserting a contracted bag portion into a vagina; inserting an insertion guide portion into the vagina together with the bag portion while sliding the insertion guide portion on a vaginal wall; and expanding the bag portion inside the vagina by fluid flowing into the bag portion through an opening/closing portion, so as to hold an intravaginal support device inside the vagina. The method further can include pressing a pressing portion to cause the fluid to flow out of the bag portion, thereby contracting the expanded bag portion; and removing the contracted bag portion and the insertion guide portion from inside the vagina.

In the treating method, preferably, the expanding the bag portion inside the vagina by the fluid flowing into the bag portion through the opening/closing portion so as to hold the intravaginal support device inside the vagina includes locking of at least part of the expanded bag portion onto part of pubic tissue through a vaginal anterior wall.

In the treating method, preferably, for example, the expanding the bag portion inside the vagina by the fluid flowing into the bag portion through the opening/closing portion so as to hold the intravaginal support device inside the vagina includes generating a tension in a direction perpendicular to a direction of going from a vaginal orifice toward the depth of the vagina, between that part of the expanded bag portion which makes contact with a vaginal anterior wall and that portion of the insertion guide portion which makes contact with a vaginal posterior wall.

In the treating method, preferably, the expanding the bag portion inside the vagina by the fluid flowing into the bag portion through the opening/closing portion so as to hold the intravaginal support device inside the vagina includes pressing of the bag portion in an expansion process by the insertion guide portion so as to promote the expansion of the bag portion in the direction of a vaginal anterior wall.

Preferably, the treating method can include a step of pressing the pressing portion to cause the fluid to flow out of the bag portion, thereby adjusting the amount of expansion of the bag portion for retaining the intravaginal support device inside the vagina.

In the treating method, preferably, the opening/closing portion has a check valve which allows fluid to flow into the bag portion but inhibits the fluid from flowing out of the bag portion, and the pressing the pressing portion to cause the fluid to flow out of the bag portion so as to contract the expanded bag portion includes pressing the pressing portion inward to open the opening/closing portion so as to allow the fluid to flow out of the bag portion.

In the treating method, preferably, the insertion guide portion is formed with a recessed portion for putting a finger therein, and the removing the contracted bag portion and the insertion guide portion from inside the vagina includes application of a force to the recessed portion in the insertion guide portion in a direction of going from the depth of the vagina toward a vaginal orifice.

According to the intravaginal support device disclosed herein, the insertion guide portion can be inserted into the vagina together with the bag portion, with the bag portion kept contracted to an appropriate degree and while sliding the insertion guide portion on the vaginal wall. In addition, by expanding the bag portion within the vagina by the fluid flowing in through the opening/closing portion, the intravaginal support device can be retained inside the vagina. According to this feature, therefore, an intravaginal support device can be obtained, which is relatively easy to insert into a vagina and which can be retained in a patient's vagina.

In the intravaginal support device, the insertion guide portion promotes the expansion of the bag portion in the direction of the vaginal anterior wall. By inserting the intravaginal support device into a vagina and causing fluid to flow into the bag portion through the opening/closing portion so as to expand the bag portion to the vaginal anterior wall side, part of the bag portion can be locked onto the pubic tissue through the vaginal anterior wall. Consequently, the intravaginal support device can be reliably retained inside the vagina of the patient.

According to the fluid injection device disclosed herein, the injection portion of the fluid injection device can be connected to the intravaginal support device inserted in a vagina, or the intravaginal support device with the injection portion of the fluid injection device connected thereto can be inserted into the vagina, and fluid can be fed in an amount adjusted by the adjusting operation portion and under pressure to the injection port of the injection portion by the injection operation portion. According to this feature, therefore, a fluid injection device can be obtained, which offers a relatively easy fluid injection operation.

BRIEF DESCRIPTION OF THE DRAWINGS

FIGS. 1A and 1B are perspective views of an intravaginal support device according to a preferred embodiment disclosed herein, wherein FIG. 1A shows an expanded state, and FIG. 1B shows a contracted state;

FIGS. 2A and 2B are longitudinal sectional views of the intravaginal support device of FIGS. 1A and 1B, wherein FIG. 2A depicts an expanded state, and FIG. 2B shows a contracted state;

FIGS. 5A and 5B are partial longitudinal sectional views illustrating a condition in which the intravaginal support device of FIGS. 1A and 1B is disposed inside a vagina, wherein FIG. 5A shows a state before expansion, and FIG. 5B shows a state after expansion;

FIGS. 8A and 8B are perspective views of showing a further modification of the intravaginal support device of FIGS. 1A and 1B, wherein FIG. 8A depicts an insertion guide portion in a state before deformation by rotation about an axis perpendicular to a direction of going from the vaginal orifice side toward the vaginal depth side, and FIG. 8B shows the insertion guide portion in a state after the deformation by rotation;

FIGS. 9A and 9B are perspective views of yet another modification of the intravaginal support device of FIGS. 1A and 1B, wherein FIG. 9A depicts an insertion guide portion in a state before deformation by rotation about an axis in a direction of going from the vaginal orifice side toward the vaginal depth side, and FIG. 9B shows the insertion guide portion in a state after the deformation by rotation;

FIG. 15 is a perspective view showing a condition in which the intravaginal support device in the expanded state of FIG. 1A and the fluid injection device of FIG. 3 are connected to each other by a tube.

DETAILED DESCRIPTION

Figure 1A:
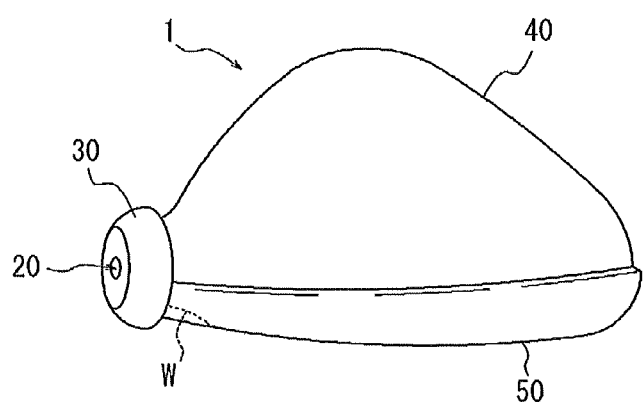

Embodiments of the present disclosure will be described below, referring to the drawings.

An intravaginal support device according to a preferred embodiment disclosed herein will first be described below, referring to FIGS. 1A, 1B, 2A, and 2B.

Figure 1B:
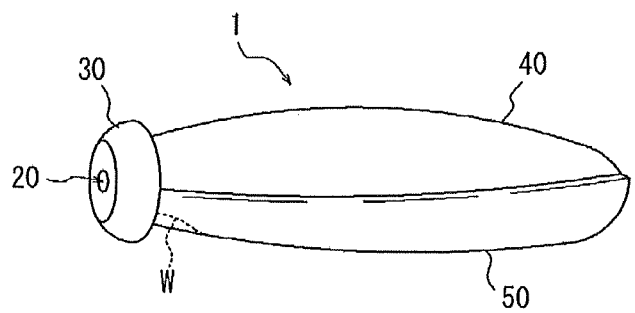
Figure 2A:
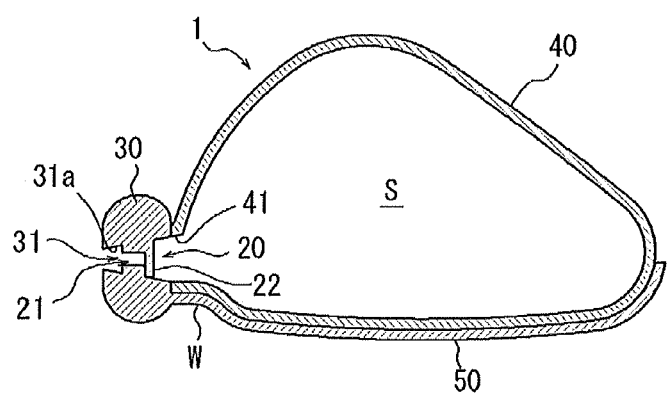
Figure 2B:
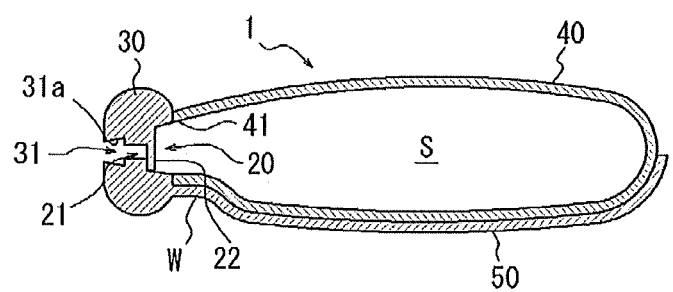

As shown in FIGS. 1A and 1B, an intravaginal support device 1 in this embodiment can include an opening/closing portion 20, a ring body (pressing portion) 30, a bag portion 40, and an insertion guide portion 50. The opening/closing portion 20 is capable of switching operations between an open state for allowing passage of fluid (in this embodiment, air) therethrough and a cut-off state for cutting off passage of the fluid. For example, as shown in FIGS. 2A and 2B, the opening/closing portion 20 has a through-hole 21 piercing between the inside and the outside of the bag portion 40. Of the through-hole 21, an opening on the bag portion 40 side is sealed with a check valve 22, which is supported in a cantilever fashion. Therefore, the opening/closing portion 20 is kept in such a state by the check valve 22 that flowing-in of air into the bag portion 40 is permitted but flowing-out of the air from inside the bag portion 40 is inhibited.

The ring body 30 is disposed to surround the opening/closing portion 20. By pressing the ring body 30 to the inside at a predetermined circumferential position to elastically deform the ring body 30, the check valve 22 can be elastically deformed so as to open the through-hole 21, and thereby air can be allowed to flow out of the bag portion 40. The ring body 30 is provided, at its side surface opposite to the bag portion 40, with a recess 31 (connecting portion) communicating with the through-hole 21. An inner peripheral wall 31a of the recess 31 is formed in an undercut shape. To the recess 31 (connecting portion) is to be connected an injection port of a fluid injection device which will be described later.

The bag portion 40 has a mouth portion 41 at an end portion on the vaginal orifice side, and forms an air storage space S communicating with the mouth portion 41. The mouth portion 41 is united with the ring body 30 by joining (bonding), for example. The bag portion 40 is formed from a gas-tight elastic material, and is capable of being expanded by flowing-in of air through the opening/closing portion 20 and contracted by flowing-out of the air through the opening/closing portion 20.

The insertion guide portion 50 is in the shape of an elliptic elongate dish extending along part of an outer surface of the bag portion 40, from a vaginal orifice side end portion to a vaginal depth side end portion of the bag portion 40. An end portion on the vaginal orifice side of the insertion guide portion 50 is united with a side surface on the bag portion 40 side of the ring body 30. In addition, the insertion guide portion 50 is provided, at its end portion on the vaginal orifice side, with a recessed portion W in which an operator's finger is to be put when removing the intravaginal support device 1 from inside a vagina. The insertion guide portion 50 can be formed from an elastic material having such a degree of elasticity that the insertion guide portion 50 can be inserted into a vagina by pushing the ring body 30 (to which the vaginal orifice side end portion of the insertion guide portion 50 is united) toward the depth of the vagina and that the patient does not feel pain when the intravaginal support device 1 is inserted into the vagina. In addition, the insertion guide portion 50 is preferably formed from an elastic material having such a degree of elasticity as to help ensure that at the time of expansion of the bag portion 40, the expansion of the bag portion 40 toward a vaginal anterior wall can be promoted by pressing the bag portion 40 by the insertion guide portion 50. Examples of preferable blank material for the insertion guide portion 50, can include, for example, elastomers, and flexible or rigid synthetic resins.

A fluid injection device according to one embodiment will be described below by way of example, referring to FIGS. 3 and 4.

Figure 3:
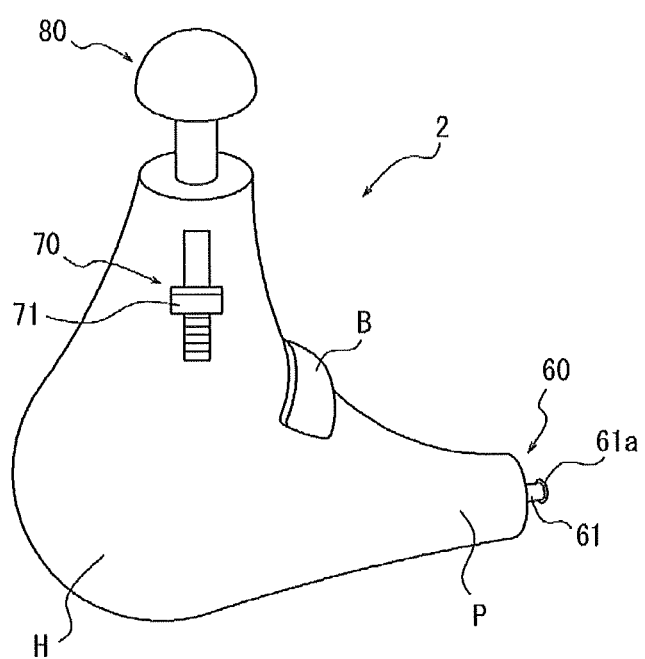
FIG. 3 is a perspective view of a fluid injection device according to a preferred embodiment disclosed herein.

As shown in FIG. 3, a fluid injection device 2 can include an injection portion 60, an adjusting operation portion 70, and an injection operation portion 80. The injection portion 60 is provided in a distal region of a projecting portion P having its distal portion so sized and shaped as to be insertable into a vagina. The injection portion 60 can be connected to the recess 31 (connecting portion) of the intravaginal support device 1 described using FIGS. 2A and 2B above. In accordance with an exemplary embodiment, the injection portion 60 has an injection port 61 for communicating with the opening/closing portion 20. For example, as illustrated in FIG. 4, the injection port 61 is formed with an annular projection 61a at an outer peripheral wall of a tip portion thereof. The annular projection 61a can be locked on the inner peripheral wall 31a (which is undercut-shaped) at the recess 31 of the intravaginal support device 1.

The injection port 61 can be locked on the recess 31 of the intravaginal support device 1 by a process in which a tip end face 60a of the injection portion 60 is abutted on a side surface, opposite to the bag portion 40, of the ring body 30 of the intravaginal support device 1. In addition, the injection port 61 is so configured that when a button B shown in FIG. 3 is depressed, the injection port 61 is withdrawn from the tip end face 60a of the injection portion 60, so as to be unlocked from the recess 31 of the intravaginal support device 1.

In accordance with an exemplary embodiment, as depicted in FIG. 3, a proximal region of the projecting portion P is bent in a roughly L-shaped form toward the adjusting operation portion 70 so that the bent portion can be used as a grasping portion H to be held by an operator's palm when inserting the intravaginal support device 1 into a vagina. Further, the projecting portion P may be provided in its distal region with marks indicative of the distance from the distal portion so that when the distal region of the projecting portion P is inserted into a vagina together with the intravaginal support device 1, the length by which the intravaginal support device 1 and the projecting portion P are inserted into the vagina can be relatively easily grasped by the user.

In addition, the adjusting operation portion 70 is so configured that it is possible by operating a lever 71 to adjust the quantity of fluid to be fed to the injection port 61 of the injection portion 60. The injection operation portion 80 is so configured that when the injection operation portion 80 is depressed, the fluid in the quantity adjusted by the adjusting operation portion 70 can be fed under pressure to the injection port 61 of the injection portion 60. Therefore, air in a desirable amount determined on the basis of diagnosis by a doctor, for example, can be easily and relatively accurately injected with good reproducibility. In addition, for example when edema of an organ is reduced or drooping of an organ is lessened as a result of continued use of the intravaginal support device 1, the quantity of fluid to be fed to the injection port 61 of the injection portion 60 may be reduced by operating the adjusting operation portion 70, whereby the intravaginal support device 1 can be properly used, without inducing a sense of excessive oppression in the patient. Similarly, when drooping of an organ is increased due to ageing, the quantity of fluid fed to the injection port 61 of the injection portion 60 can be increased by operating the adjusting operation portion 70, whereby the holding force for the organ by the intravaginal support device 1 can be enhanced, and the symptom can be suppressed. Further, such an adjustment value of the adjusting operation portion 70 itself suggests an improvement or worsening of the disease, which helps enable the doctor to read variations in the patient's pelvic organ prolapse from the transition of the adjustment value of the adjusting operation portion 70.

Figure 5A:
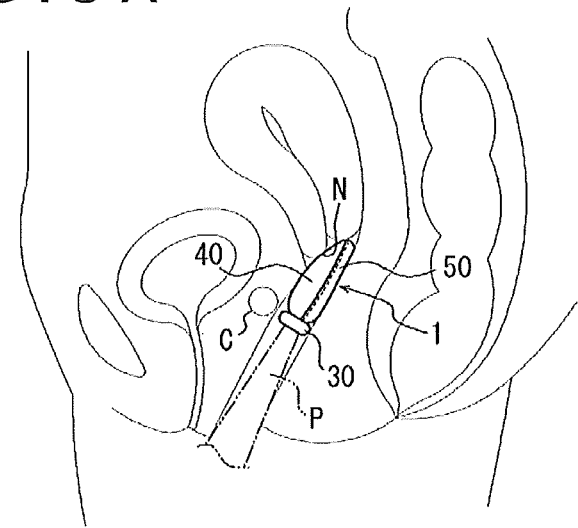

According to the configurations of the intravaginal support device of the embodiment disclosed herein and the fluid injection device of the embodiment disclosed herein, the amount of air fed to the injection port 61 of the injection portion 60 can preliminarily be adjusted by operating the lever 71 of the adjusting operation portion 70 so that air in a desired amount determined on the basis of diagnosis by the doctor, for example, will be injected. Then, with the bag portion 40 of the intravaginal support device 1 kept in an appropriately contracted state, and with the injection portion 60 connected to the recess 31 (connecting portion) of the intravaginal support device 1, the ring body 30 of the intravaginal support device 1 can be inserted into a vagina as shown in FIG. 5A together with a distal region of the projecting portion P, while pushing the ring body 30 with the distal region of the projecting portion P. In this instance, the insertion guide portion 50 can be inserted into the vagina together with the bag portion 40 while sliding on the vaginal wall, so that the insertion of the intravaginal support device 1 can be facilitated.

Figure 4:
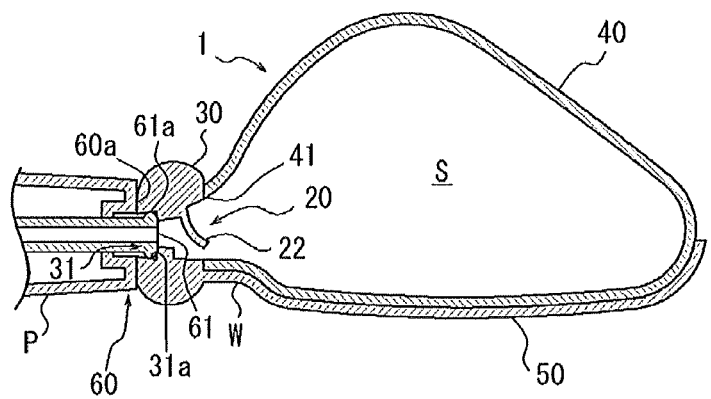
FIG. 4 is a longitudinal sectional view illustrating a condition in which the fluid injection device of FIG. 3 is connected to the intravaginal support device of FIGS. 1A and 1B and air is being injected.

When the injection operation portion 80 of the fluid injection device 2 is pushed in in a condition where the intravaginal support device 1 is inserted in a vagina, air in an amount adjusted by the adjusting operation portion 70 can be fed under pressure to the injection port 61 of the injection portion 60, and, as shown in FIG. 4, the check valve 22 of the opening/closing portion 20 can be opened, thereby to make the air flow into the bag portion 40 and to expand the bag portion 40. In this instance, it is possible for the intravaginal support device 1, with the insertion guide portion 50 disposed on the vaginal posterior wall side, to restrain expansion of the bag portion 40 in the direction of the vaginal posterior wall and, on the other hand, promote expansion of the bag portion 40 in the direction of the vaginal anterior wall (namely, to control the expanding direction of the bag portion 40 asymmetrically with respect to a direction perpendicular to the direction of going from the vaginal orifice side toward the vaginal depth side).

Figure 5B:
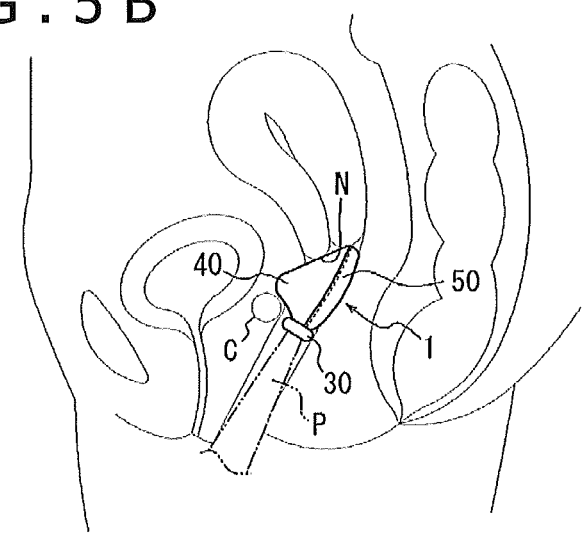

In accordance with an exemplary embodiment, the expanding direction of the bag portion 40 when air is uniformly injected into the bag portion 40 by the fluid injection device 2 can be controlled so that the degree of expansion is greater on the vaginal anterior wall side than on the vaginal posterior wall side. By expanding the bag portion 40 more on the vaginal anterior wall side than on the vaginal posterior wall side, part of the bag portion 40 can be pushed into that region in the vaginal anterior wall which is in the vicinity of pubic tissue C on the uterine neck N side (specifically, that region between the pubic tissue C and the uterine neck N which is nearer to the pubic tissue C than to the uterine neck N), as depicted in FIG. 5B. As a result, part of the bag portion 40 is locked on the pubic tissue C through the vaginal anterior wall, whereby the intravaginal support device 1 can be securely held inside the vagina.

In addition, since the insertion guide portion 50 makes contact with the vaginal posterior wall over a wide area, the pressure exerted on the rectum at the time of expansion of the bag portion 40 can be alleviated, and dyschezia which might occur in conjunction with the use of the intravaginal support device 1 can be mitigated or avoided.

Then, by depressing the button B of the fluid injection device 2 to unlock the fluid injection device 2 and the intravaginal support device 1 from each other and remove the distal region of the projecting portion P of the fluid injection device 2 from inside the vagina, part of the bag portion 40 can be locked on the pubic tissue C through the vaginal anterior wall, as shown in FIG. 5B. With part of the bag portion 40 thus locked on the pubic tissue C through the vaginal anterior wall, it is ensured that even upon generation of a force on the intravaginal support device 1 in the direction of going from the vaginal depth side toward the vaginal orifice side, a resisting force in the direction of going from the vaginal orifice side toward the vaginal depth side can be generated. Consequently, the intravaginal support device 1 can be reliably held inside the vagina, the uterine neck N can be supported by the intravaginal support device 1 from below, and/or drooping of the vaginal anterior wall can be inhibited, and/or drooping of the vaginal posterior wall can be inhibited, and thereby to reliably inhibit pelvic organ prolapse.

Further, at the time of removing the intravaginal support device 1 from inside the vagina, the patient can contract the intravaginal support device 1 by pressing the ring body 30 to the inside at a predetermined circumferential position with a finger, and can draw out the intravaginal support device 1 by putting in a hooking manner a finger in the recessed portion W of the insertion guide portion 50 or on the ring body 30.

Note that the intravaginal support device 1 may not necessarily be inserted into a vagina by use of the aforementioned fluid injection device 2, and may be inserted by pushing the ring body 30 toward the vaginal depth side with a finger. In that case, with the intravaginal support device 1 inserted in the vagina, the injection portion 60 of the aforementioned fluid injection device 2 is inserted into the vagina and the injection port 61 is made to communicate with the opening/closing portion 20, whereby the bag portion 40 of the intravaginal support device 1 can be expanded. In this case, therefore, the fluid injection device 2 is not limited to the one configured to have the projecting portion P as aforementioned; for example, a fluid injection device 2 configured to interconnect the injection port 61 and the adjusting operation portion 70 by a flexible tube, for example, can be adopted.

A method of using the intravaginal support device 1 will be described below.

In using the intravaginal support device 1 disclosed herein, there are carried out: a first step of inserting the bag portion 40 in a contracted state into a vagina; a second step of inserting the insertion guide portion 50 into the vagina together with the bag portion 40 while sliding the insertion guide portion 50 on the vaginal wall; a third step of expanding the bag portion 40 inside the vagina by fluid flowing into the bag portion 40 through the opening/closing portion 20, to thereby hold the intravaginal support device 1 inside the vagina; a fourth step of pressing the pressing portion 30 to cause the fluid to flow out of the bag portion 40, thereby contracting the expanded bag portion 40; and a fifth step of removing the contracted bag portion 40 and the insertion guide portion 50 from inside the vagina.

At the time of inserting the intravaginal support device 1 into the vagina in the second step, the user must insert the bag portion 40 to a predetermined position in the vagina while partly pushing up a drooping organ. In this case, the insertion guide portion 50 having elasticity is inserted into the vagina together with the bag portion 40 while sliding on the vaginal wall, whereby the bag portion 40 being flexible due to being in a contracted state can be easily inserted to a predetermined position in the vagina without being pushed back by the drooping organ.

At the time of expanding the bag portion 40 in the third step, the insertion guide portion 50 presses the bag portion 40 in the expansion process, thereby to promote expansion of the bag portion 40 in the direction of the vaginal anterior wall. Then, at least part of the expanded bag portion 40 comes into contact with pubic tissue C by way of the vaginal anterior wall. In this instance, the insertion guide portion 50 disposed on the opposite side from that part of the bag portion 40, which makes contact with the vaginal wall makes contact with the vaginal posterior wall. As a result, between that part of the bag portion 40 which is in contact with the vaginal anterior wall and that part of the insertion guide portion 50 which is in contact with the vaginal posterior wall, there is generated a tension in a direction perpendicular to the direction of going from the vaginal orifice toward the depth of the vagina. Here, since the insertion guide portion 50 is in contact with the vaginal posterior wall over a wide area, the insertion guide portion 50 serves as a footing for generation of a sufficient tension for retaining the intravaginal support device 1 inside the vagina, and permits at least part of the expanded bag portion 40 to be easily locked on the pubic tissue C through the vaginal anterior wall. In addition, since the contact between the insertion guide portion 50 and the vaginal posterior wall takes place over an extensive area, the intravaginal support device 1 can be inserted into the vagina while mitigating a local and excessive pressure, which might be exerted on the rectum by the expanded bag portion 40. Such functions of the insertion guide portion 50 and the bag portion 40 can help enable the user to position the intravaginal support device 1 inside the vagina, without any special operation and under a condition where the intravaginal support device 1 is unlikely to be dislodged from inside the vagina even in the case where a force in the direction of going from the depth of the vagina toward the vaginal orifice is exerted on the intravaginal support device 1 from a drooping organ.

In the fourth step, starting from the condition where the bag portion 40 of the intravaginal support device 1 is expanded, the expanded bag portion 40 can be contracted by pressing the pressing portion 30 in the vagina so as to cause the fluid to flow out of the bag portion 40. Such a feature can help enable the user to adjust the bag portion 40 to an appropriate expansion amount by causing the fluid to partly flow out of the bag portion 40, in the case where, for example, the user has injected a more than necessary amount of fluid into the bag portion 40 by mistake and the bag portion 40 has been thereby expanded excessively. There may be a case where the expansion amount of the bag portion 40 needed for supporting a drooping organ is reduced due to daily variations in the degree of drooping of the organ, an improvement of the disease itself, variations in the drooping position attendant on ageing, and/or where the patient gets a sense of discomfort or pain if the intravaginal support device 1 is used with the bag portion 40 expanded to the same degree as before. In such a situation, by causing the fluid to partly flow out of the bag portion 40, the bag portion 40 can be adjusted to an appropriate expansion amount such that the sense of discomfort or pain is removed. Further, for example in removing the intravaginal support device 1 from inside the vagina, the removal can be facilitated by compressing the pressing portion 30 within the vagina so as to cause the fluid to flow out of the bag portion 40 until the bag portion 40 is contracted. Naturally, where the bag portion 40 of the intravaginal support device 1 has been contracted within the vagina, the bag portion 40 can be expanded inside the vagina again by causing the fluid to flow into the bag portion 40 through the opening/closing portion 20. Therefore, the bag portion 40 can be again expanded, in the case where excessive flow-out of the fluid from the bag portion 40 has been caused by mistake, or in the case where the expansion amount of the bag portion 40 must be increased for inhibition of drooping of an organ, because of daily variations or worsening of the disease itself. In accordance with an exemplary embodiment, such a feature can help enable the user to adjust the overall size of the intravaginal support device 1 while feeling a variation in resistance inside the vagina due to a variation in the degree of expansion/contraction of the bag portion 40, in the condition where the intravaginal support device 1 is kept inserted in the vagina.

At the time of contracting the expanded bag portion 40 in the fourth step, the pressing portion 30 being formed of an elastic material is pressed to the inside within the vagina, whereby the check valve 22 also formed of an elastic material is elastically deformed together with the pressing portion 30, and the fluid is caused to flow out of the bag portion 40. In addition, in the case where the recessed portion W in which to put a finger in a hooking manner for removing the intravaginal support device 1 from inside the vagina is formed in the insertion guide portion 50 and where the recessed portion W is provided in the vicinity of the pressing portion 30, the user is able, by putting a finger in the recessed portion W in a hooking manner, to simultaneously press the pressing portion 30 with the finger. Therefore, simultaneously when the user puts a finger in the recessed portion W in a hooking manner and pulls it for removing the intravaginal support device 1 from inside the vagina, the pressing portion 30 and the check valve 22 can be elastically deformed, thereby causing the fluid to flow out of the bag portion 40. In accordance with an exemplary embodiment, such a feature can help enable the user to easily accomplish both the contraction of the bag portion 40 (the fourth step) and the removal of the intravaginal support device 1 from inside the vagina (the fifth step), by only carrying out the operation of putting a finger in the recessed portion W in a hooking manner and pulling it.

A method of using the intravaginal support device 1 together with the fluid injection device 2 will be described below.

At the time of using the intravaginal support device 1 together with the fluid injection device 2, there are conducted: a first step of connecting the intravaginal support device 1 and the fluid injection device 2 in the exterior of a patient's body; a second step of pushing in the fluid injection device 2, with the intravaginal support device 1 and the fluid injection device 2 in the connected state, to insert part of the fluid injection device 2 as well as the bag portion 40 and the insertion guide portion 50 of the intravaginal support device 1 into the vagina while sliding the insertion guide portion 50 on the vaginal wall; a third step of operating the fluid injection device 2 so as to expand the bag portion 40 by the fluid flowing in through the opening/closing portion 20 and thereby to hold the intravaginal support device 1 inside the vagina; and a fourth step of detaching the fluid injection device 2 from the intravaginal support device 1 within the vagina.

In the first step, the connection of the intravaginal support device 1 and the fluid injection device 2 to each other in the exterior of the patient's body can include a process in which the injection port 61 of the fluid injection device 2 opens the opening/closing portion 20 by way of the connection, to make the inside of the fluid injection device 2 and the inside of the bag portion 40 communicate with each other.

In the second step, with the intravaginal support device 1 and the fluid injection device 2 kept in the connected state, the fluid injection device 2 is pushed in, whereby part of the fluid injection device 2 and the bag portion 40 and the insertion guide portion 50 of the intravaginal support device 1 are together inserted into the vagina while sliding the insertion guide portion 50 on the vaginal wall. Such a configuration can help enable the user to easily control the position of the intravaginal support device 1 within the vagina by extracorporeally grasping and operating the fluid injection device 2 connected to the intravaginal support device 1. Due to the position of the vaginal orifice/vagina in the body, it can be difficult for the user to directly confirm her vaginal orifice through visual observation or, after inserting an article entirely into the vagina, to securely grasp part of the article within the vagina and control its position. Therefore, in the case of using the intravaginal support device 1 singly, as in the case where the user is not well accustomed or in other similar cases, it may be difficult to swiftly insert the intravaginal support device 1 into the vagina, or to operate the intravaginal support device 1 within the vagina while grasping part of the intravaginal support device 1 after the intravaginal support device 1 is entirely inserted into the vagina. In accordance with an exemplary embodiment, in the case of using the intravaginal support device 1 in the state of being connected to the fluid injection device 2, the user can visually confirm the degree of insertion of the intravaginal support device 1 into the vagina, on the basis of the movement of the fluid injection device 2 largely exposed outside the user's body. In addition, both in the case where the intravaginal support device 1 is located inside the vagina and in the case where the intravaginal support device 1 is located outside the vagina, the fluid injection device 2 can be stably grasped on an extracorporeal basis, so that it is possible to control easily and precisely the position of the intravaginal support device 1 at the time of insertion into the vagina and while the intravaginal support device 1 is located within the vagina. Furthermore, since the intravaginal support device 1 disclosed herein can include the insertion guide portion 50 which has an appropriate degree of elasticity, the position of the intravaginal support device 1 can be easily adjusted within the vagina in response to the operation of the fluid injection device 2, which can make it relatively easy to be inserted the intravaginal support device 1 deeper into the vagina, and to lock the bag portion 40 of the intravaginal support device 1 on the pubic tissue C through the vaginal anterior wall in the third step.

In the third step, the user adjusts the amount of fluid fed to the injection port 61, by preliminarily operating the adjusting operation portion 70 of the fluid injection device 2. Then, the user operates the injection operation portion 80 to pressure feed the fluid in the amount adjusted by the adjusting operation portion 70, causing the fluid to flow from the fluid injection device 2 through the opening/closing portion 20 of the intravaginal support device 1 into the bag portion 40, and thereby expanding the bag portion 40 of the intravaginal support device 1.

The fluid injection device 2 disclosed herein can be used in a state in which the injection port 61 of the fluid injection device 2 and the opening/closing portion 20 of the intravaginal support device 1 are connected to each other by use of a separately provided tube (see FIG. 15, in which the tube is denoted by numeral 90). In this case, at least part of the tube 90 on the side where the tube 90 can be connected to the opening/closing portion 20 must be configured to have such a diameter as to be insertable into the vagina. In an exemplary procedure using such a configuration, the user preliminarily connects the intravaginal support device 1 and the fluid injection device 2 to each other by use of the tube 90 on an extracorporeal manner to insert into a vagina the whole body of the intravaginal support device 1 and part of the tube 90. Thereafter, the fluid injection device 2 is operated so that an appropriately adjusted amount of fluid is caused to flow from the injection port 61 of the fluid injection device 2 and through the lumen of the tube 90 and the opening/closing portion 20 of the intravaginal support device 1 into the bag portion 40 of the intravaginal support device 1. After the expanded bag portion 40 is locked on the pubic tissue C through the vaginal anterior wall, the tube 90 is detached from the intravaginal support device 1. In this case, the fluid injection device 2 and the tube 90 may be in the connected state or in a disconnected state. Such a configuration makes it possible to design the fluid injection device 2 in a smaller size, which allows the fluid injection device 2 to be relatively easily carried out.

In place of the aforementioned intravaginal support device 1, a variety of modifications may be adopted.

Figure 6:
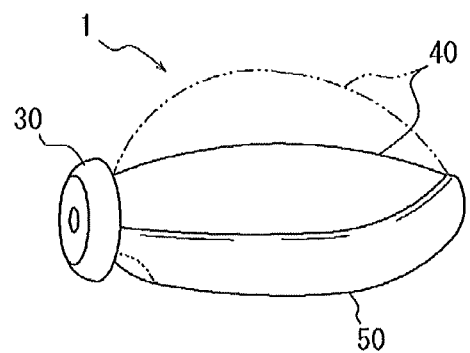
FIG. 6 is a perspective view showing a modification of the intravaginal support device of FIGS. 1A and 1B, depicting an example in which an insertion guide portion is curved.
Figure 7:
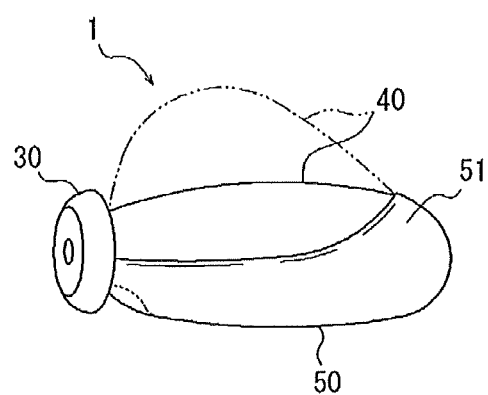
FIG. 7 is a perspective view showing another modification of the intravaginal support device of FIGS. 1A and 1B, illustrating an example in which an insertion guide portion is provided with a covering portion.
Figure 8A:
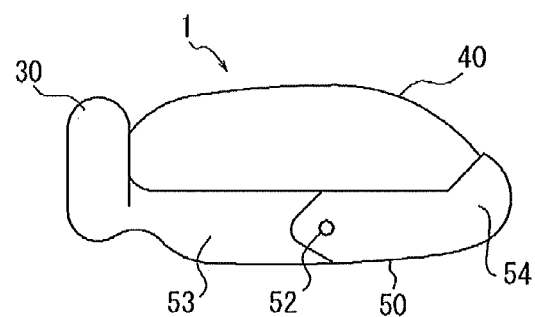
Figure 8B:
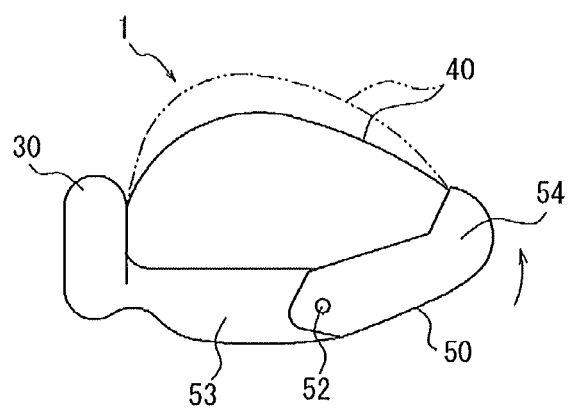

For instance, while the insertion guide portion 50 is in the shape of an elliptic elongate dish extending from the vaginal orifice side toward the vaginal depth side in the embodiment shown in FIGS. 1A to 2B, such a shape is not restrictive. For example, as shown in FIG. 6, the insertion guide portion 50 may be in the shape of an elliptic elongate dish, which is curved in the direction of the vaginal anterior wall, from the vaginal orifice side toward the vaginal depth side. Such a structure can help ensure that when the intravaginal support device 1 is inserted into the depth of the vagina, a vaginal depth side portion of the insertion guide portion 50 comes into the state of being inclined toward the vaginal anterior wall in relation to the direction of going from the vaginal orifice side toward the vaginal depth side. Therefore, at the time of expanding the bag portion 40, the expansion of the bag portion 40 can be promoted toward the region in the vicinity of the pubic tissue C on the uterine neck N side, which is shown in FIGS. 5A and 5B. In addition, as shown in FIG. 7, the insertion guide portion 50 may be provided with a covering portion 51, which covers entirely a vaginal depth side end portion of the bag portion 40. In this case, by preliminarily adjusting the shape of the covering portion 51, the expanding direction of the bag portion 40 can be controlled toward the vaginal anterior wall side. Note that in FIGS. 6 and 7, the solid line denoted by numeral 40 depicts an appropriately contracted state of the bag portion 40 at the time of insertion into the vagina, and the alternate long and two short dashes line denoted by numeral 40 depicts an expanded state of the bag portion 40 after the insertion into the vagina. In FIGS. 8A to 14 referred to in the following description, also, the states of the bag portion 40 will be depicted in the same manner as in FIGS. 6 and 7.

In addition, as shown in FIGS. 8A and 8B or FIGS. 9A and 9B, the insertion guide portion 50 may be composed of two members which are relatively rotatable through a shaft. In an example shown in FIGS. 8A and 8B, the insertion guide portion 50 is composed of two members 53 and 54, which are relatively rotatable through a shaft 52 perpendicular to the direction of going from the vaginal orifice side toward the vaginal depth side. Therefore, when the intravaginal support device 1 has arrived in the depth of the vagina, the member 54 on the vaginal depth side is rotated about the shaft 52 from the vaginal posterior wall side toward the vaginal anterior wall side, as indicated by arrow in FIG. 8B. As a result, at the time of expanding the bag portion 40, it is possible to promote expansion of the bag portion 40 toward the vaginal anterior wall side. In addition, the insertion guide portion 50 can be deformed in accordance with variations in the angle of the insertion direction within the vagina, in the course from the vaginal orifice to the depth of the vagina. Consequently, the sense of discomfort can be alleviated at the time of insertion of the intravaginal support device 1.

Figure 9A:
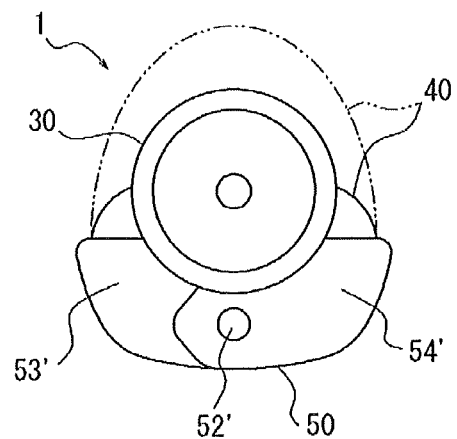
Figure 9B:
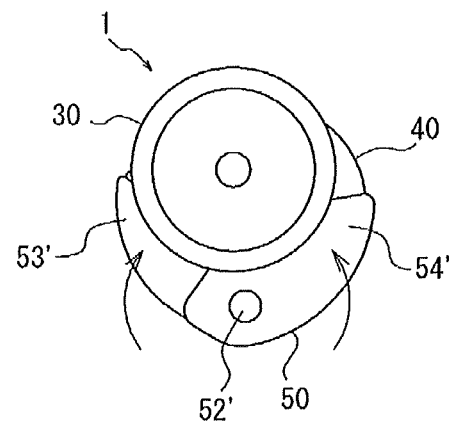

In an example illustrated in FIGS. 9A and 9B, the insertion guide portion 50 is composed of two members 53' and 54' which are relatively rotatable through a shaft 52' extending in the direction of going from the vaginal orifice side toward the vaginal depth side. Therefore, at the time of inserting the intravaginal support device 1 into the vagina, starting from the state depicted in FIG. 9A the two members 53' and 54' can be relatively rotated and folded about the shaft 52', as indicated by arrow in FIG. 9B. Accordingly, the intravaginal support device 1 as a whole can be reduced in outside diameter, so that the insertion of the intravaginal support device 1 into the vagina can be made easier. In addition, since the two members 53' and 54' can be relatively rotatable about the shaft 52', by expanding the bag portion 40 of the intravaginal support device 1, the bag portion 40 can push open the members 53' and 54', for transition from the state depicted in FIG. 9B to the state shown in FIG. 9A.

Figure 10:
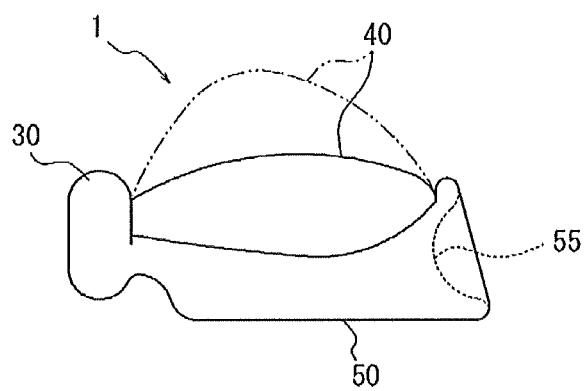
FIG. 10 is a perspective view of a yet further modification of the intravaginal support device of FIGS. 1A and 1B, illustrating an example in which an insertion guide portion is provided with a hollow.

In addition, as shown in FIG. 10, the insertion guide portion 50 may be formed, in its end portion on the vaginal depth side, with a hollowed portion 55 which is adaptable to the uterine neck. Such a configuration can help ensure that at the time of inserting the intravaginal support device 1 into the vagina, the intravaginal support device 1 as a whole can be inserted into the vagina while a drooping uterine neck is being pressed in by the hollowed portion 55.

Figure 11:
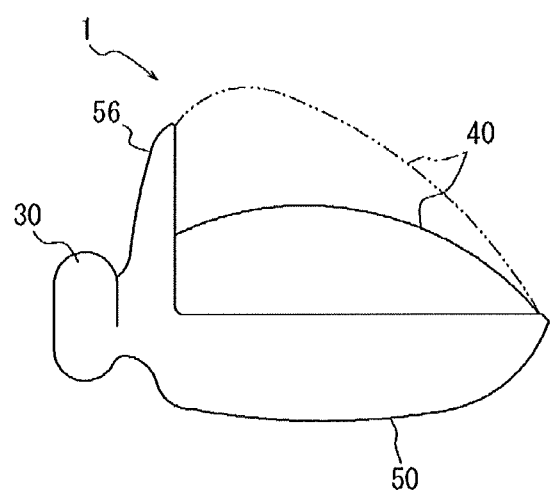
FIG. 11 is a perspective view of still another modification of the intravaginal support device of FIGS. 1A and 1B, depicting an example in which an insertion guide portion is provided with a locking piece.

In addition, as shown in FIG. 11, the insertion guide portion 50 may be formed, at its end portion on the vaginal orifice side, with a locking piece 56 for locking onto the pubic tissue C (illustrated in FIGS. 5A and 5B) through the vaginal anterior wall. In this case, at the time of expansion of the bag portion 40, that portion of the bag portion 40 which is on the vaginal anterior wall side can push in that region of the vaginal anterior wall in the vicinity of the pubic tissue C which is on the uterine neck N side, and the bag portion 40 can be thereby locked on the pubic tissue C through the locking piece 56 and the vaginal anterior wall.

In the case of using the intravaginal support device 1 having the insertion guide portion 50 provided with the locking piece 56 as an aid for locking of the intravaginal support device 1 to the pubic tissue C, the intravaginal support device 1 is inserted into the vagina so as to lock the locking piece 56 of the insertion guide portion 50 to the pubic tissue C through the vaginal anterior wall. In this procedure, the user advances the whole body of the intravaginal support device 1 toward the vaginal depth side while keeping the insertion guide portion 50 in contact with the vaginal posterior wall. At the stage where the locking piece 56 has advanced beyond part corresponding to the pubic tissue C, the user moves the insertion guide portion 50 so that its distal portion located on the vaginal depth side is slightly lifted up, whereby the locking piece 56 can be efficiently locked on the pubic tissue C through the vaginal anterior wall.

Figure 12:
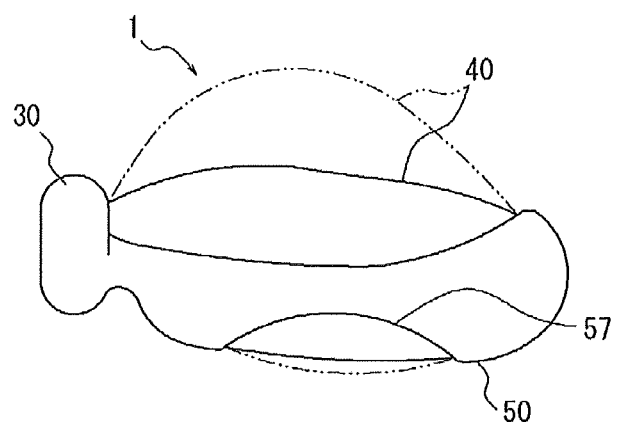
FIG. 12 is a perspective view of a still further modification of the intravaginal support device of FIGS. 1A and 1B, showing an example in which an insertion guide portion is provided with an opening.

In addition, as shown in FIG. 12, the insertion guide portion 50 may be formed with an opening 57 for permitting protrusion of the bag portion 40 and adapting the protruding bag portion 40 to the vaginal posterior wall, whereby it is possible to restrain drooping of the vaginal posterior wall and to enhance a therapeutic effect on rectal prolapse. In accordance with an exemplary embodiment, for example, at the time of expansion of the bag portion 40, the bag portion 40 protruding via the opening 57 presses and supports the vaginal posterior wall, whereby an inhibitory effect on drooping of the vaginal posterior wall can be obtained, in addition to inhibition of drooping of the vaginal anterior wall by the locking of the bag portion 40 onto the pubic tissue C. Therefore, a therapeutic effect on a patient suffering from pelvic organ prolapse attended by rectal prolapse arising mainly from drooping of the vaginal posterior wall can be enhanced. In addition, the opening 57 formed in the insertion guide portion 50 constitutes a recessed portion in which a finger can be put in a hooking manner when the bag portion 40 is contracted. Accordingly, the opening 57 can be used also as a hooking portion where a finger is to be put in a hooking manner at the time of removing the intravaginal support device 1 from inside the vagina.

Figure 13:
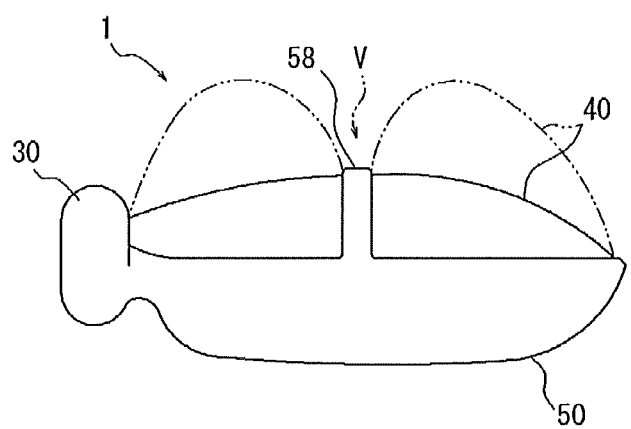
FIG. 13 is a perspective view of another modification of the intravaginal support device of FIGS. 1A and 1B, depicting an example in which an insertion guide portion is provided with an expansion restraining portion.

In addition, as shown in FIG. 13, the insertion guide portion 50 may be provided with an expansion inhibitory portion 58 which covers part of a vaginal anterior side region of the bag portion 40. This configuration can help ensure that the shape of the bag portion 40 when expanded can be adjusted in conformity with the internal shape of the patient's vagina. In addition, this configuration makes it possible to form a fitting recess V that can fit to the pubic tissue C (depicted in FIGS. 5A and 5B) through the vaginal anterior wall.

Figure 14:
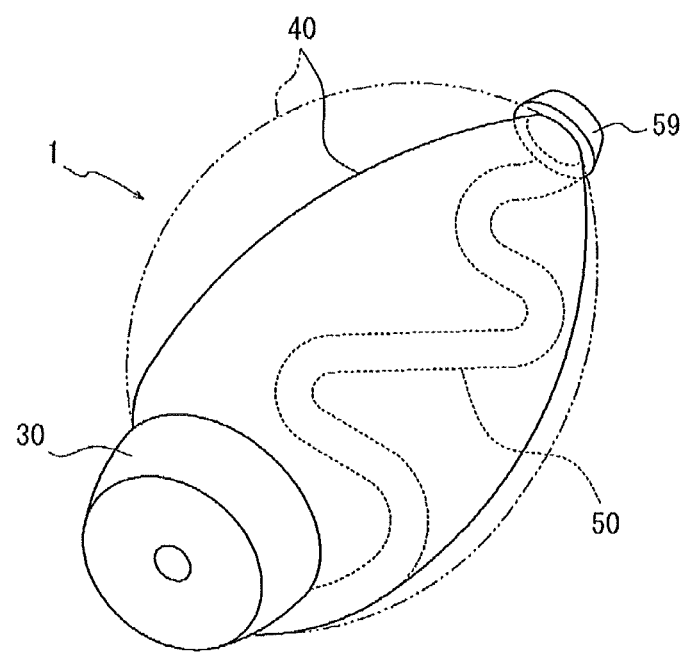
FIG. 14 is a perspective view of a further modification of the intravaginal support device of FIGS. 1A and 1B, illustrating an example in which an insertion guide portion is tortuous in shape.

Furthermore, as shown in FIG. 14, a configuration may be adopted in which the insertion guide portion 50 is in a tortuous shape along an outer surface of the bag portion 40 from a vaginal orifice side end portion to a vaginal depth side end portion of the bag portion 40, a vaginal orifice side end portion of the insertion guide portion 50 is integral with the ring body 30, and the insertion guide portion 50 is provided at a vaginal depth side end portion thereof with a bag retaining portion 59 for retaining the vaginal depth side end portion of the bag portion 40. According to such a configuration, the insertion guide portion 50 as a whole can be provided with stretchability in the insertion direction. Therefore, at the time of inserting the intravaginal support device 1 into the vagina while pushing a drooping uterine neck into the vagina, the force with which the uterine neck is pushed in can be regulated, whereby the sense of discomfort at the time of insertion of the intravaginal support device 1 can be alleviated. In addition, at the time of removing the intravaginal support device 1 from inside the vagina, a finger can be put in a hooking manner on any of the tortuously curved parts of the insertion guide portion 50. Therefore, the labor for groping around for a hooking part can be alleviated, and the removal of the intravaginal support device 1 from inside the vagina can be facilitated. In addition, the material cost for the insertion guide portion 50 can be reduced.

In addition, as shown in FIG. 15, a configuration may be adopted in which the intravaginal support device 1 in the expanded state as shown in FIG. 1A and the fluid injection device 2 as shown in FIG. 3 are interconnected by a tube 90. This configuration produces the effects as mentioned earlier herein.

The foregoing is a mere presentation of an embodiment of the present disclosure, and various changes and modifications could be effected therein by one skilled in the art without departing from the spirit or scope of the disclosure as defined in the appended claims. For instance, while the ring body 30 has been described as being contiguous with the vaginal orifice side end portion of the insertion guide portion 50, this is not restrictive. The ring body 30 may be provided to be integral with the mouth portion 41 of the bag portion 40, and the insertion guide portion 50 may be joined to an outer surface of the bag portion 40 by an adhesive, for example. In that case, in inserting the intravaginal support device 1 into the vagina, the vaginal orifice side end portion of the insertion guide portion 50 is pushed by a finger toward the vaginal depth side, whereby the bag portion 40 can be guided into the vagina by the insertion guide portion 50. Consequently, the intravaginal support device 1 can be inserted into the vagina. In addition, the expression of the first to fifth steps in using the intravaginal support device 1 and the expression of the first to fourth steps in using the intravaginal support device 1 together with the fluid injection device 2 are each a mere presentation of an exemplary procedure, not limitative of the order in which the steps are to be carried out The detailed description above describes an intravaginal support device, fluid injection device, and treating method for pelvic organ prolapse by use of intravaginal support device. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A method for mitigating a symptom of pelvic organ prolapse utilizing an intravaginal support device, the method comprising:
    inserting an insertion guide into a vagina together with a contracted bag while sliding the insertion guide on a vaginal posterior wall, the insertion guide arranged on at least part of an outer surface of the contracted bag and extending from a vaginal orifice side end of the contracted bag to a vaginal depth side end of the contracted bag;
    expanding the contracted bag inside the vagina to form an expanded bag by fluid flowing into the contracted bag through an opening such that a degree of expansion is greater on a vaginal anterior wall side of the expanded bag than a vaginal posterior wall side of the expanded bag, so as to hold the intravaginal support device inside the vagina and wherein a maximally extended part of the expanded bag extends into a region in a vaginal anterior wall between a pubic tissue and a uterine neck; and
    directly supporting the uterine neck from below with the expanded bag of the intravaginal support device.

2. The method according to claim 1, comprising:
    compressing a ring-shaped body to a predetermined circumferential position to cause the fluid to flow out of the expanded bag, thereby contracting the expanded bag; and
    removing the contracted bag and the insertion guide from inside the vagina.

3. The method according to claim 2, comprising:
    forming the insertion guide with a recess for putting a finger in the recess.

4. The method according to claim 3, wherein the removing the contracted bag and the insertion guide from inside the vagina comprises:
    applying a force to the recess in the insertion guide in a direction from a depth of the vagina toward a vaginal orifice.

5. The method according to claim 2, comprising:
    pressing the ring-shaped body to cause the fluid to flow out of the expanded bag, thereby adjusting an amount of expansion of the expanded bag for retaining the intravaginal support device inside the vagina.

6. The method according to claim 2, comprising:
    allowing the fluid to flow into the contracted bag and inhibiting the fluid from flowing out of the expanded bag with a check valve in the opening.

7. The method according to claim 1, wherein the expanding the contracted bag inside the vagina by the fluid flowing into the contracted bag through the opening so as to hold the intravaginal support inside the vagina comprises:
    locking the maximally extended part of the expanded bag extending into the region in the vaginal anterior wall between the pubic tissue and the uterine neck into place.

8. The method according to claim 1, wherein the expanding the contracted bag inside the vagina by the fluid flowing into the contracted bag through the opening so as to hold the intravaginal support inside the vagina comprises:
    generating a tension in a direction perpendicular to a direction of going from a vaginal orifice toward a depth of the vagina, between the expanded bag which makes contact with the vaginal anterior wall and the insertion guide which makes contact with the vaginal posterior wall.

9. The method according to claim 1, wherein the expanding the contracted bag inside the vagina by the fluid flowing into the contracted bag through the opening so as to hold the intravaginal support inside the vagina comprises:
    pressing of the contracted bag during expansion by the insertion guide so as to promote the expansion of the contracted bag in a direction of the vaginal anterior wall.

10. The method according to claim 1, wherein the insertion guide has an elliptical elongated shape.

11. The method according to claim 1, further comprising:
    providing the insertion guide with a cover, which covers an entirety of the vaginal depth side end of the contracted bag;
    wherein the inserting the insertion guide into the vagina together with the contracted bag is accomplished with a fluid injection device;
    wherein the fluid flowing into the contracted bag is injected by the fluid injection device; and
    controlling an expanding direction of the contracted bag with the cover.

12. The method according to claim 1, wherein the insertion guide is composed of two members, which are relatively rotatable through a shaft, the method further comprising:
    rotating a member of the members on a vaginal depth side of the vagina about the shaft from the vaginal posterior wall toward the vaginal anterior wall; and
    promoting expansion of the contracted bag toward the vaginal anterior wall.

13. A method for mitigating a symptom of pelvic organ prolapse utilizing an intravaginal support device, the method comprising:
    inserting the intravaginal support device into a vagina, the intravaginal support device including an insertion guide together with a contracted bag and a ring-shaped body surrounding an opening of the intravaginal support device, the insertion guide arranged on at least part of an outer surface of the contracted bag and extending from a vaginal orifice side end of the contracted bag to a vaginal depth side end of the contracted bag;
    pushing the ring-shaped body toward a depth of the vagina to dispose the insertion guide on a vaginal posterior wall in a region between a pubic tissue and a uterine neck;
    expanding the contracted bag inside the vagina to form an expanded bag by fluid flowing into the contracted bag through the opening such that a degree of expansion is greater on a vaginal anterior wall side of the expanded bag than a vaginal posterior wall side of the expanded bag, so as to hold the intravaginal support device inside the vagina and wherein a maximally extended part of the expanded bag extends into a vaginal anterior wall in the region between the pubic tissue and the uterine neck; and directly supporting the uterine neck from below with the expanded bag of the intravaginal support device.

14. The method according to claim 13, comprising:

compressing the ring-shaped body to a predetermined circumferential position to cause the fluid to flow out of the expanded bag, thereby contracting the expanded bag; and removing the contracted bag and the insertion guide from inside the vagina.

15. The method according to claim 13, wherein the expanding the contracted bag inside the vagina by the fluid flowing into the contracted bag through the opening so as to hold the intravaginal support inside the vagina comprises:

fixing the maximally extended part of the expanded bag extending into the vaginal anterior wall in the region between the pubic tissue and the uterine neck into place.

16. The method according to claim 13, wherein the expanding the contracted bag inside the vagina by the fluid flowing into the contracted bag through the opening so as to hold the intravaginal support inside the vagina comprises:

generating a tension in a direction perpendicular to a direction of going from a vaginal orifice toward the depth of the vagina, between the expanded bag which makes contact with the vaginal anterior wall and the insertion guide which makes contact with the vaginal posterior wall.

17. The method according to claim 13, wherein the expanding the contracted bag inside the vagina by the fluid flowing into the contracted bag through the opening so as to hold the intravaginal support inside the vagina comprises:

pressing of the contracted bag during expansion by the insertion guide so as to promote the expansion of the contracted bag in a direction of the vaginal anterior wall.

18. The method according to claim 13, comprising:

compressing the ring-shaped body to cause the fluid to flow out of the expanded bag, thereby adjusting an amount of expansion of the expanded bag for retaining the intravaginal support device inside the vagina.

19. The method according to claim 13, comprising:

allowing the fluid to flow into the contracted bag and inhibiting the fluid from flowing out of the expanded bag with a check valve in the opening.

20. The method according to claim 13, wherein the insertion guide has an elliptical elongated shape.

\* \* \* \* \*